United States Patent [19]
Pirkl et al.

[11] Patent Number: 5,616,818
[45] Date of Patent: Apr. 1, 1997

[54] PROCESS FOR THE POLYNITRATION OF AROMATIC COMPOUNDS

[75] Inventors: Hans-Georg Pirkl, Köln; Reinhard Schomäcker, Leverkusen; Uwe Klingler, Dormagen; Thomas Schieb, Rösrath; Gerhard Wiechers, Leverkusen, all of Germany; Jürgen Zimmermann, Walnut Creek, Calif.

[73] Assignee: Bayer Aktiengesellschaft, Leverkusen, Germany

[21] Appl. No.: 543,095

[22] Filed: Oct. 13, 1995

[30] Foreign Application Priority Data

Oct. 17, 1994 [DE] Germany .................... 44 37 047.4

[51] Int. Cl.$^6$ .................................................. C07C 205/06
[52] U.S. Cl. ........................... 568/932; 568/934; 568/935
[58] Field of Search .................................. 568/932, 934, 568/935

[56] References Cited

U.S. PATENT DOCUMENTS

| | | | |
|---|---|---|---|
| 2,256,999 | 9/1941 | Castner | 260/645 |
| 3,160,669 | 12/1964 | Terao et al. | 260/645 |
| 3,928,475 | 12/1975 | Dassel | 260/645 |
| 3,981,935 | 9/1976 | McCall | 260/645 |
| 4,021,498 | 5/1977 | Alexanderson et al. | 260/645 |
| 4,091,042 | 5/1978 | Alexanderson et al. | 260/645 |
| 4,361,407 | 11/1982 | Pellegrini | 366/340 |
| 4,596,699 | 6/1986 | Desgrandchamps et al. | 422/160 |
| 4,647,212 | 3/1987 | Hankison | 366/165 |
| 4,918,250 | 4/1990 | Mason et al. | 568/934 |
| 4,973,770 | 11/1990 | Evans | 568/929 |
| 4,994,242 | 2/1991 | Rae et al. | 422/224 |
| 4,996,004 | 2/1991 | Bücheler et al. | 252/314 |
| 5,001,272 | 3/1991 | Mason | 568/934 |

(List continued on next page.)

FOREIGN PATENT DOCUMENTS 272974  6/1988  European Pat. Off. .

OTHER PUBLICATIONS

Albright et al: ACS Symposium Series 22, American Chemical Society (1976), 190–209.
Chemical Abstracts, vol. 82, 1975, Ref. 85882e (Month Unavailable).
Roy B. Moodie et al, Electrophilic Aromatic Substitution. Part 36.1, Kinetics of Aromatic Nitrations in Solutions of Dinitrogen Pentaoxide and of Nitronium Salts in Nitric Acid. In: J. Chem. Soc. Perkin Trans. 2, (Month unavailable) 1990, S. 833–836.
James F. Johnston et al, $^{15}$N Nuclear Polarisation in Nitration and Related Reactions. Part 5.$^1$ The Borderline between the Classical and the Electron Transfer Mechanisms in Nitration by the Nitronium Ion. In J. Chemc. Soc. Perkin Trans. 2, (Month unavailable) 1991, S. 623–628.
Roy B. Moodie et al, Electrophilic Aromatic Substitution. Part 37.1 Products of Aromatic Nitrations of some Chloronitrobenzens and Substituted Benzoic Acids in Solutions of Dinitrogen Pentaoxide and of Nitronium Salts in Nitric Acid. In: J. Chem. Soc. Perkin Trans. 2, (Month unavailable) 1991, S. 645–650.

Primary Examiner—Samuel Barts
Attorney, Agent, or Firm—Joseph C. Gil; Lyndanne M. Whalen

[57] ABSTRACT

An aromatic compound is polynitrated in a continuous process in a single apparatus under adiabatic conditions in an emulsion as the reaction medium. From 1.3 to 3.5 mol of $HNO_3$ per mol of aromatic compound are introduced in the form of a nitronium ion solution into the reactor with the aromatic compound under conditions such that an emulsion forms. The emulsion, which has a tendency to coalesce, is maintained by repeated dispersion. The first dispersion of the liquid streams to produce the emulsion takes place in less than one second. At least 20% of the total amount of $HNO_3$ to be used should generally be present during this first dispersion. It is preferred, however, that the total amount of nitronium ion solution to be used be present at the time the aromatic compound and nitronium ion solution are first dispersed.

19 Claims, 2 Drawing Sheets

U.S. PATENT DOCUMENTS

| | | | |
|---|---|---|---|
| 5,057,632 | 10/1991 | Imm et al. | 568/934 |
| 5,099,078 | 3/1992 | Quakenbush | 568/934 |
| 5,099,080 | 3/1992 | Quakenbush | 568/934 |
| 5,116,536 | 5/1992 | Bücheler et al. | 252/314 |
| 5,117,048 | 5/1992 | Zaby et al. | 560/347 |
| 5,245,092 | 9/1993 | Quakenbush | 568/934 |
| 5,313,009 | 5/1994 | Guenkel et al. | 568/927 |
| 5,345,012 | 9/1994 | Schieb et al. | 568/934 |

PROCESS FOR THE POLYNITRATION OF AROMATIC COMPOUNDS

BACKGROUND OF THE INVENTION

The present invention relates to a continuous process for the direct production of polynitrated aromatic compounds by reacting an aromatic compound with a solution containing nitronium ions.

The production of nitrated aromatics has been the subject of numerous publications and patents. It has been known since 1846 that aromatic compounds can be converted to the corresponding substituted aromatic compounds with a mixture of sulfuric and nitric acid (i.e., the so-called mixed acid or nitrating acid). Musspratt & Hofmann, *Liebigs Ann. Chem.*, Volume 57, page 201 (1846).

Nitrobenzene, dinitrobenzene, nitrochlorobenzene, nitrotoluene and dinitrotoluene have for many decades been commercially produced isothermally in stirred-tank reactors or in tubular reactors with a mixed acid composed of sulfuric acid and nitric acid. After a phase separation between the organic and aqueous phase, the nitrated aromatic product is recovered and the sulfuric acid is concentrated by evaporation of water at elevated temperature. Until now, polynitrations (for example dinitrations) have been carried out industrially by means of a two-step isothermal nitration. See, e.g., Kirk-Othmer, *Encyclopedia of Chemical Technolgy*, 3rd Edition, Volume 15 (1981) and Ullmann, *Encyclopedia of Industrial Chemistry*, Volume A17, pages 411–455 (VCH Weinheim (1991)).

The continuous (mono)nitration of aromatics has been described in detail in the prior art. See, e.g., Groggins, *Unit Processes in Organic Chemistry* (McGraw-Hill, New York (1958)). Mixed acids or separate streams of sulfuric acid and nitric acid together with, for example, benzene are fed into a stirred nitrator. The two-phase reaction mixture is stirred continuously and intensively cooled in order to conduct the reaction as isothermally as possible. From the nitrator this mixture is passed to another stirred-tank reactor connected in series, or is fed directly into a separator where the phases are separated. There the organic product phase is separated from the aqueous sulfuric acid phase and worked up. The sulfuric acid diluted by the water in the nitric acid and by the water of reaction has to be returned to the reactor as concentrated acid, with considerable expenditure of energy. In the polynitration of an aromatic compound, this energy-consuming concentration process is carried out in each individual, tandem-arranged, isothermal mononitration. In the dinitration of toluene, for example, the sulfuric acid may optionally be fed from the dinitration stage to the mononitration stage, so that only one concentration of sulfuric acid is necessary.

The physical and chemical data for these industrial nitrating conditions and the model concepts for nitration using nitronium ion solutions are discussed in the literature. See, for example, Hansen et al, *Chem. Eng. Sci.*, Volume 32, page 775 (1977); Albright et al, *ACS Symposium Series* 22, page 201 (American Chemical Society (1976); Albright et al, *J. App. Chem. Biotechnol.*, Volume 26, page 522 (1976); and Urbanski, *Chemistry and Technology of Explosives*, Volume 1 (MacMillan, New York (1964)).

The nitration is carried out in a two-phase reaction (organic aromatic phase and aqueous nitrating acid phase) essentially in the aqueous phase, so that the solubility of the aromatics in the aqueous phase, the rate of mass transfer from phase to phase and the intrinsic rate of reaction together influence the conversion rate observed as a whole. There thus exists a complex reaction system the rate of which is controlled kinetically or by the mass transfer, depending on how the reaction is conducted.

A model for the aromatic mononitration was formulated by Albright et al. and described in *ACS Symposium Series* 22, page 201 (American Chemical Society (1976)). This model was as follows:
a) unnitrated aromatic compound diffuses out of the organic phase along the organic/aqueous phase interface;
b) unnitrated aromatic compound dissolves and diffuses from the organic/aqueous phase interface into the aqueous phase;
c) nitric acid diffuses out of the interior of the aqueous phase in the direction of the phase interface;
d) while the aromatic compound permeates into the aqueous phase and the $HNO_3$ diffuses counter to it out of the interior of the aqueous phase, the aromatic compound reacts with $HNO_3$ to form a nitroaromatic compound and water;
e) the nitroaromatic compound formed diffuses back through the aqueous phase along the phase interface;
f) the nitroaromatic compound formed dissolves along the phase interface and diffuses from the phase interface into the interior of the organic phase; and
g) water formed diffuses from the site of formation into the interior of the aqueous phase.

Since the conventional isothermal mononitration processes are not the most energy efficient because the heat of reaction is first dissipated by cooling and the subsequent concentration of the acid requires a high energy input, early consideration was given to conducting the process adiabatically.

In U.S. Pat. No. 2,256,999 (1941) an adiabatic mononitration of several aromatic compounds such as benzene, is proposed as a new nitration process. Essential features of this prior art process are that one or more stirred-tank reactors are charged with a stoichiometric excess of the compound to be nitrated and consequently the nitric acid in the reactor is completely consumed. The sulfuric acid is then separated, concentrated using the heat of reaction and recycled to the reactor. The proportion of sulfuric acid used in the mixed acid is between 68 and 76 wt. %.

In U.S. Pat. No. 4,021,498 (1977), a process for adiabatic mononitration with an excess of nitric acid at mixing temperatures of between 40° and 80° C., sulfuric acid contents of from 60 to 70 wt. % and a maximum temperature below 145° C. is described.

In U.S. Pat. No. 4,091,042 (1978), the conditions disclosed for operating the reactor are limited specifically to the mononitration of benzene. The operation is carried out using an excess of benzene of about 10 mol % as compared with contents of $HNO_3$ and $H_2SO_4$ of from 58.5 to 66.5 wt. %.

Adiabatic, continuous processes for the production of mononitroaromatic compounds have been described in U.S. Pat. Nos. 2,256,999 (1941); 4,021,498 (1977); and 4,091,042 (1978).

Alternatively, according to U.S. Pat. No. 3,928,475 (1975) and U.S. Pat. No. 3,981,935 (1976), the heat of nitration may be used by feeding benzene vapor and nitric acid to a stirred-tank reactor containing sulfuric acid and removing the vaporizing products, water and nitrobenzene together with benzene in vapor form from the reactor. In each of the disclosed processes, the heat of reaction is used to remove water. At least some of the heat reaction is wasted, however, in vaporizing large quantities of the educt and recycling it in condensed form.

EP-A 0,373,966 (1988; corresponds to U.S. Pat. No. 4,973,770) describes a process for the mononitration of organic substances using mixed acid which employs a droplet-producing liquid jet of organic material for mixing the two phases. The use of a liquid jet for liquid/liquid mixing during the mononitration is known. (See, e.g., U.S. Pat. No. 3,160,669 (1964).) The process disclosed in EP-A 0,373,966 is carried out using a deficit of $HNO_3$, so that the aromatic compound is not completely nitrated in the reactor. In the one Example given, a conversion of only 55.3% for $HNO_3$ and 52.5% for benzene is obtained in a reactor into which benzene is injected through a nozzle.

EP-A 0,436,443 (1990; corresponds to U.S. Pat. No. 5,313,009) discloses a continuous, adiabatic nitration process in which a mixed acid containing at least 55 mol % of $H_2SO_4$ with 0% of $HNO_3$ and at least 82 mol % of $H_2SO_4$ with 18% of $HNO_3$ is used. A nitration process in which an excess of aromatic compound (as compared with $HNO_3$) is used is also claimed. In the description of the invention, it is emphasized that dinitration is to be avoided.

All of the above-described disclosures directed to adiabatic nitration processes focus on benzene in the actual Examples given and describe possible ways of conducting a process for a mononitration. More extensive nitrations are considerably more difficult to control because far more drastic reaction conditions and conditions for concentrating the sulfuric acid are necessary than is the case in a mononitration of, for example, benzene. See, e.g., Urbanski, *Chemistry and Technology of Explosives*, Volume 1 (MacMillan, New York (1964)). The second and especially the third nitro group are harder to introduce into an aromatic ring than is the first. So until now, higher temperatures and greater acid concentrations have been used for the isothermal production of diaromatics than for monoaromatics. See, e.g, Ullmann, *Encyclopedia of Industrial Chemistry*, Volume A17, pages 411–455 (VCH Weinheim (1991)).

In U.S. Pat. No. 5,001,272 (1989), a process for the production of a dinitrated aromatic compound is disclosed for the first time. Toluene is successfully converted to dinitrotoluene by means of highly concentrated aqueous nitric acid without other additives. High molar excesses of $HNO_3$, and moderate temperatures of between 40° and 70° C. are necessary for this disclosed process.

U.S. Pat. Nos. 4,918,250 (1989) and 5,057,632 (1990) and WO-A 92/06937 (1990) disclose a two-step process for the nitration of toluene via the separate nitrotoluene intermediate step to form the end product dinitrotoluene. These disclosed processes are carried out using a high molar excess of highly-concentrated nitric acid for the dinitration.

U.S. Pat. Nos. 5,099,078 (1990); 5,099,080 (1991) and 5,245,092 (1992) each disclose a process for the dinitration of toluene using highly concentrated nitric acid in a single apparatus. In U.S. Pat. No. 5,099,080 (1991) a high molar excess of $HNO_3$ is used ($HNO_3$:toluene equals from 12:1 to 9:1) and nitration is carried out at temperatures of from 0° to 90° C. In the process described in U.S. Pat. No. 5,245,092 (1992), the molar excess of $HNO_3$ is even higher.

A continuous adiabatic process for dinitration with a mixed acid in which the heat of reaction is used to evaporate water in the nitric acid and in the product was disclosed for the first time in DE-A 4,238,390 (1993). In this disclosed nitration process, a nitric acid/sulfuric acid mixture which contains a proportion by weight of $H_2SO_4$ of from 60 to 90%, a proportion by weight of $HNO_3$ of from 5 to 20% and a molar ratio of $HNO_3$/toluene of at least 2.0 is used. No detailed information with respect to the reactor used is, however, given. It is stated in the Examples that toluene is successfully nitrated to dinitrotoluene in a thin tubular reactor having an internal diameter of 0.6 mm or 0.99 mm and a length of 20 m. A stoichiometric excess of $HNO_3$ relative to toluene (molar ratio 2.15:1.0) is added and the yield is more than 99% dinitrotoluene (DNT). Mononitrotoluenes and trinitrotoluene are reported in very small quantities (<1%). In the Examples, the reactor is operated at flow rates of from 1 to 3 l/h with very high pressure losses. Such pressure losses are technically difficult to control. The scale-up of a reactor of this type having laminar flow would be possible only by duplicating the single thin tubular reactors disclosed therein. This would, however, be very expensive. The advantage of the adiabatic mode of operation is reduced because of high heat losses due to the reactor construction which heat losses can be limited only by expensive insulation measures.

In heterogeneous reaction systems such as the systems in which aromatic compounds are nitrated using a mixed acid, inhibition of the rate of reaction frequently occurs due to mass transfer from one phase into the other. It is taught in *Chem.-Ing.-Techn.*, Volume 56, pages 552–553 (1984) that two immiscible liquids can be finely distributed in each other as droplets by means of a pressure nozzle. The great increase in the interface between the two liquids makes it possible for chemical reactions between reactants in different phases to proceed more rapidly. The more finely dispersed the phases are distributed, the greater the increase in rate of reaction. High energy input into a two-phase system (e.g., through a nozzle) disperses a liquid jet into small drops immediately after leaving the nozzle orifice. Experimental results show that the sizes of the droplets in the disperse phase can be calculated from the energy input of any mixing device and from the data on the properties of the two liquids. Suitable mixing devices for dispersion are known. Examples of suitable mixing devices include jet mixers, static mixers and dynamic mixers. The most advantageous device will vary depending on the dispersion requirements. See, e.g., Ullmann, *Encyclopedia of Industrial Chemistry*, Volume B4, pages 561–586 (VCH Weinheim (1992)) and Koglin et al, *Chem.-Ing.-Techn.*, Volume 53, pages 641–647 (1981).

Reduction of undesirable by-products in complex reaction systems comprising several parallel or successive reactions by micromixing the educts at a rate which is faster than the rate at which the educts react with one another has been described in the literature. See, for example, Ullmann ,*Encyclopedia of Industrial Chemistry*, Volume B2, Chapter 24 (VCH Weinheim (1992)); Bourne & Maire, *Chem. Eng. Process*, Volume 30, page 23 (1991); and Brodkey, *Chem. Eng. Commun.*, Volume 8, page 1 (1981). If the chemical reaction rates and the rates of mixing the educts are of the same order of magnitude, then there is a complex interaction between the kinetics of the reactions and the local mixing behavior (the latter determined by the turbulence) in the reactor and around the mixing device. If the reaction rates are significantly faster than the mixing rates, the yields are clearly influenced by the mixing, that is, by the local velocity and concentration of the reactants and therefore by the construction of the reactor and the turbulence structure. See, e.g., Brodkey (ed.), *Turbulence in Mixing Operations—Theory and Application to Mixing and Reaction* (Academic Press, New York, (1975)).

Suitable devices for the rapid mixing of two liquid streams are described in many literature references and patents. See, e.g., Ullmann, *Encyclopedia of Industrial Chemistry*, Volume B4, pages 561–586 (VCH Weinheim (1992)). Many special devices have been developed for liquid/liquid mixing. Examples of such special devices are disclosed in U.S. Pat. Nos. 4,596,699; 4,647,212; and 4,361,407 and also EP-A 272,974. Special mixing devices for the adiabatic mononitration of benzene in tubular reactors have been disclosed in EP-A 0,373,966 and U.S. Pat. No. 4,994,242.

The device disclosed in U.S. Pat. No. 4,994,242 is a tubular reactor equipped with spherical redispersing baffles made of tantalum. Redispersing elements in the form of perforated plates, bubble plates, valve trays, dispersers, homogenizers, dynamic mixers, etc. are known to be useful for carrying out two-phase reactions. See, e.g., Schröder et al, *Chem.-Ing.-Techn*, Volume 56, pages 552–553 (1981); Koglin et al, *Chem.-Ing.-Techn*, Volume 53, pages 641–647 (1981); and Koglin, *Maschinemarkt*, Volume 86, pages 346–350 (1980). U.S. Pat. No. 4,994,242 discloses a dispersing element characterized by high stability with minimum use of material (tantalum).

SUMMARY OF THE INVENTION

It is an object of the present invention to provide a process for the adiabatic polynitration of aromatic compounds which may be carried out commercially using a mixed acid nitrating agent in a single reactor.

It is also an object of the present invention to provide a process for the adiabatic polynitration of aromatic compounds in residence times which may be less than 10 minutes.

It is a further object of the present invention to provide a process for the direct polynitration of an aromatic compound.

It is another object of the present invention to provide a process for the direct polynitration of aromatic compounds under reaction conditions such that decomposition of the product and energy costs are minimized.

These and other objects which will be apparent to those skilled in the art are accomplished by reacting an aromatic compound with a nitronium ion solution in an emulsion as the reaction medium. The nitronium ion solution is used in an amount such that from 1.3 to 3.5 mol of nitric acid is present for each mol of aromatic compound to be nitrated. This process is carried out on a continuous basis in a single reactor under adiabatic conditions.

DETAILED DESCRIPTION OF THE PRESENT INVENTION

Figure 1:
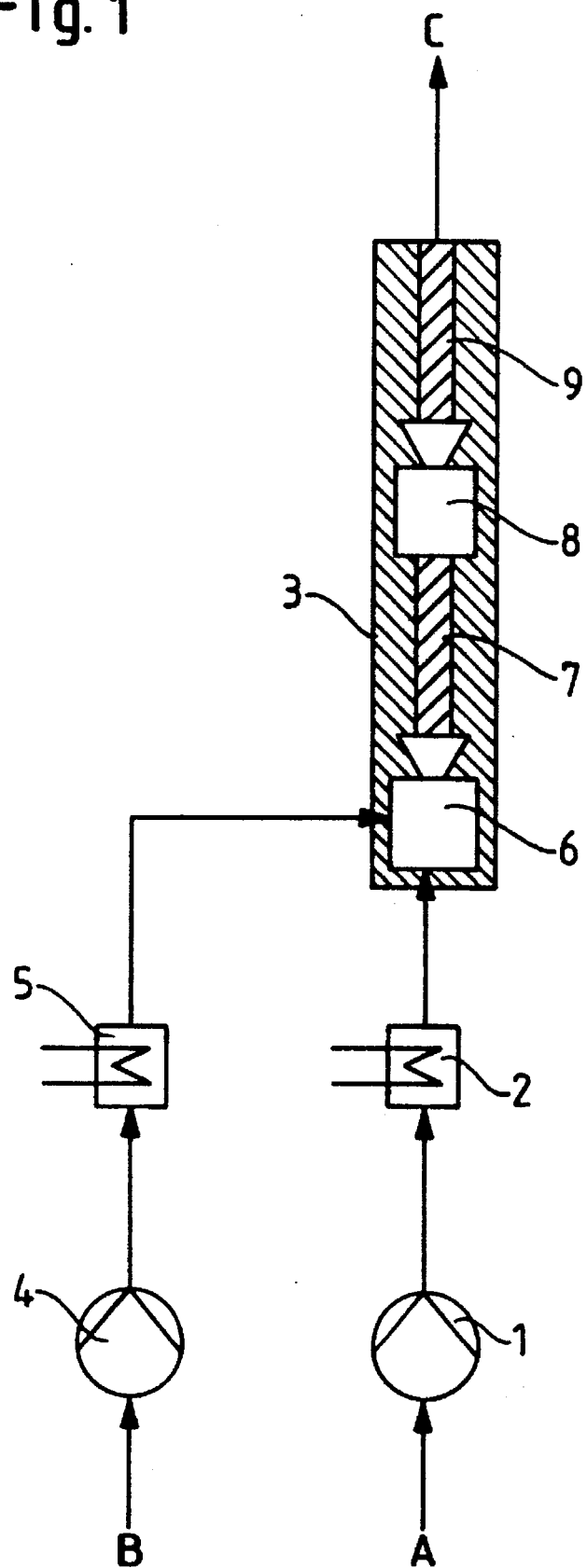
FIG. 1 is a diagram of a two-stage nozzle tubular reactor system which is useful for carrying out the process of the present invention.

It has now been found that polynitration of aromatic compounds can be carried out in a single apparatus under adiabatic reaction conditions using a mixed acid as nitrating agent. The polynitration of all aromatic compounds by this process is, in principle, possible in residence times of less than 10 minutes.

The present invention provides a process for the continuous, adiabatic production of polynitrated aromatic compounds in a multinitrator. This process is conducted in a single apparatus. The aromatic compound and nitronium ion solution are used in quantities such that the molar ratio of $HNO_3$ to aromatic compound is from about 1.3 to about 3.5. The aromatic compound is polynitrated (i.e., dinitrated or nitrated to a higher degree). In this process, the first dispersion of the educt streams to produce an emulsion as the reaction medium is conducted in less than one second to minimize the inhibition by mass transfer and the formation of by-products (for example, nitrobenzoic acids, nitrocresols) during the extremely rapid first nitration. A high specific phase interface is maintained by recurrent redispersion of the emulsion, which has a tendency to coalesce, in order to achieve a high space-time yield. Trinitrated aromatic compounds can also be produced by this method.

In another embodiment of the present invention, the nitronium ion solution can also be fed in subdivided portions to the reactor. Preferred inlet points for these split streams are, apart from the nozzle for the first dispersion, the redispersing devices of the individual reactor stages along the axis of the reactor. The nitronium ion solutions used in this embodiment of the present invention preferably differ from one another in their composition. The nitric acid content of the individual split streams can be between 0 and 30 wt. %. The stream of nitronium ions used for the first dispersion in this embodiment of the present invention should contain at least 20% of the entire amount of $HNO_3$ to be fed to the reactor.

The reactor used in the process of the present invention is made up of reaction stages in series, which are adjusted in accordance with the prevailing reaction rates and inhibitions by mass transfer. Because of the extremely sharply decreasing reaction rate from mononitration to trinitration via dinitration, suitable measures must be taken for the optimal operation of the reaction process. Use of a single reactor makes it possible for the mononitration to be carried out at very high nitration rates. To avoid an undesirably high yield of by-products, it is necessary to bring the two immiscible phases into very close contact by dispersion and to emulsify them in each other in less than one second. All types of mixers are suitable for the dispersion of aromatic compounds in mixed acid. Suitable mixers are known and have been described in the literature and in patents. See, e.g., Ullmann, *Encyclopedia of Industrial Chemistry*, Volume B4, pages 561–586 (VCH Weinheim (1992)); Ullmann, *Encyclopedia of Industrial Chemistry*, Volume B2, Chapter 24 (VCH Weinheim (1992)); and Perry's *Chemical Engineers' Handbook*, 6th ed., pages 21–61 (McGraw-Hill, New York (1984)). Preferred devices for the rapid emulsification of the educt streams in each other include jet mixers, static mixers and dynamic mixers.

Particularly preferred devices for the rapid mixing of the educts and to start the exothermic nitration reaction are jet mixers. Jet mixers have the added advantages of hermetic sealing, variably adjustable mixing performance and global plug flow characteristics. Preferred geometries for jet mixers are described in EP-A 0,101,007 (1982) and DE 3,744,001.

In a preferred embodiment of the present invention, the educts are emulsified in a rapidly mixing apparatus of the jet mixer type in order to lessen undesirable side reactions and the strongly exothermic first nitration is carried out simultaneously and/or in succession. The heat liberated in the first nitration reaction is stored in the reaction mixture and preferably not released to the surroundings.

In a particularly preferred embodiment of the present invention, the intensity of mixing in the jet mixer is selected so that almost all of the mononitration takes place in the reactor followed by the dinitration. The temperature of the reaction mixture during the mononitration has a decisive influence on the distribution of isomers after the dinitration.

In accordance with the present invention, the first dispersion of the reactants to form an emulsion as the reaction medium is successfully performed in a jet mixer with a specific energy input of from about 10 to about 10,000 joules per liter, preferably from about 50 to about 2,000 J/l, most preferably from about 100 to about 1,000 J/l. The repeated redispersion of the coalescing emulsion is carried out by means of jet mixers, static mixers and dynamic mixers, preferably at a specific energy input of from 1 to 1,000 joules per liter, more preferably from about 10 to about 200 J/l.

The control of the selectivity of the nitration through the intensity of the dispersion (i.e., through the varying inhibition by mass transfer of the chemical reactions) is of great importance particularly in directing substituents on the aromatic ring (for example, in toluene and chlorobenzene). In a preferred embodiment of the present invention, the immiscible phases are emulsified in each other in less than one second. The fine droplets of emulsion in turbulent flow which are produced by the specific energy input provide for an extremely rapid exchange of substances between organic and aqueous phase, bring about a successive mononitration and dinitration and largely avoid a simultaneous mononitration and dinitration which results in higher average mononitrating temperatures and diminished selectivity in many aromatic compounds. The mononitration is terminated by the rapid first dispersion and fine emulsification in less than 30 seconds, preferably less than 15 seconds.

Two-phase reactions with a desirable, virtually complete conversion with respect to one component must be carried out with a minimum residence time in a reactor which mixes the two components in order to achieve a high space-time yield. Devices of this type are known in a variety of forms. See, e.g., Ullmann, *Encyclopedia of Industrial Chemistry*, Volume B4, pages 87–120 (VCH Weinheim (1992)). Suitable devices for the simultaneous dispersion with guaranteed minimum residence time include: a hold-up tube with dynamic mixers, a hold-up tube with static mixers, a hold-up tube with jet mixers, stirred-tank reactors in series, a bubble column, a multistage jet mixer and combinations of these reactors.

The preferred device for the dinitration or polynitration in accordance with the present invention is a combination of a jet mixer with a tubular reactor having static mixing units. Due to the narrow range of residence times, the required hold-up of the reactor is minimal and the quantity of hot nitrating acid can be kept small. A device of this kind is hermetically sealed and can be manufactured economically from glass-lined steel, glass and/or tantalum.

A particularly preferred device for carrying out the nitration is a tubular reactor equipped with recurring static mixers or jet mixers as redispersing units. These recurring sections made up of a hold-up tube equipped with redispersing units are referred to as reactor stages. In a particularly preferred embodiment, the initial mixing is carried out using a jet mixer which produces a fine emulsion in a tubular reactor having from 2 to 30 redispersing stages. Preferred redispersing units are different structural forms of perforated trays or perforated plates which finely redisperse the coalescing emulsion, preferably at a specific energy input of from about 1 to about 1,000 joules per liter, most preferably at from about 10 to about 200 J/l.

The mixing performance may, during the course of the process of the present invention, decrease with the increasing conversion of the aromatic compound along the longitudinal axis of the reactor because the reaction rate falls progressively. The rate of exchange of substances increases due to the increasingly better solubility of the aromatic compounds, higher diffusion rate and increased stability of the emulsion as a result of the droplets of polynitrated aromatic compound which increasingly stabilize the interfaces. It is therefore possible in a most particularly preferred embodiment to reduce the redispersing performance in the upper part of the reactor by making the distance between the redispersing stages greater, by less intensively dispersing structural units or by using lower flow rates in the tubular reactor and/or in the redispersing unit. The residence time between the individual redispersing stages is, in accordance with the invention, determined by the rate of coalescence of the emulsion. High space-time yields can be achieved only by avoiding a complete separation of the phases prior to renewed redispersion. The residence time between the dispersion stages in accordance with the present invention is therefore between about 0.2 and about 60 seconds. In a preferred embodiment, from about 0.5 to about 15 seconds is the average residence time between the dispersion stages.

For a more directed control of the nitrating conditions of the individual reaction stages, the nitronium ion solution can be split and fed in varying concentration to the tubular reactor. The composition of the mixed acid can be varied in order to obtain a more favorable temperature and nitric acid content along the axis of the reactor than in a process in which the nitronium ion solution is not split, and thereby improve the selectivity of the nitration. In a particularly preferred procedure, the split stream is also introduced into the reactor using a jet mixer. At least 20% of the entire amount of $HNO_3$ to be used is used for the first dispersion of the nitronium ion solution and aromatic compound.

Adiabatic polynitration in accordance with the present invention is far superior to the conventional two-step isothermal nitration for the production of dinitroaromatic compounds because the control of temperature and hence of energy takes place entirely through the composition of the educt streams and their temperatures. Such temperature control in combination with the short residence times in the reactor (up to 10 minutes, preferably less than 5 minutes, most preferably less than 3 minutes), enable very easy and rapid control of an adiabatic polynitration process of this kind via the educt streams.

In the process of the present invention, the nitronium ion solutions used are mixed acids which contain nitric acid and at least one of the following acids: acetic acid, phosphoric acid, perchloric acid, trifluoromethane-sulfonic acid, and sulfuric acid. Preferred nitronium ion solutions are mixed acids of nitric acid, acetic acid, phosphoric acid and sulfuric acid. Mixed acids in which these individual acids are replaced by larger constituent quantities of the remaining acids are also preferred. The most preferred nitronium ion solution is made up of only aqueous nitric acid and sulfuric acid.

Where the nitronium ion solution is not split into fractions, the preferred mixed acid is composed of nitric acid and sulfuric acid and contains from about 80 to about 100 wt. % of inorganic constituents which include from about 60 to about 95 wt. % of $H_2SO_4$, from about 1 to about 20 wt. % of $HNO_3$ and at least 3 wt. % of $H_2O$. The mixture also contains up to 20 wt. % of organic constituents which are from about 70 to about 100 wt. % of polynitrated aromatics with the remainder being by-products.

In accordance with the present invention, the molar ratio between aromatic compound and nitric acid in the mixed acid is selected on the basis of the desired degree of nitration. The molar ratio of $HNO_3$ to aromatic compound in this solution should be maintained at from about 1.3 to about 3.5, preferably from about 1.5 to about 3.0 and most preferably from about 1.7 to about 2.5.

If a complete dinitration of the aromatic compound is to be achieved, a molar ratio of $HNO_3$ to aromatic compound of 2.0 is theoretically necessary. Molar ratios of from about 1.3 to about 3.5, preferably molar ratios of from about 1.5 to about 3.0 and most preferably molar ratios of from about 1.7 to about 2.5 are suitable in practice. Stoichiometry and composition of the mixed acid determine the quantities of the aqueous and organic phases and the adiabatic rise in temperature in the reactor.

The temperature of the reactor is determined by the mixing temperature and by the adiabatic rise in temperature of the highly exothermic reaction. In the process of the present invention, the temperature is generally between 50° and 200° C. In a preferred embodiment, the mixing temperature of the reactants in the reactor inlet is between 80° and 150° C., preferably between 100° and 130° C., and the temperature of the products flowing out is between 130° and 200° C., preferably between 140° and 180° C. In another preferred embodiment, in which significantly more $HNO_3$ is added to the nitronium ion solution as compared with the first embodiment of the invention, the mixing temperature of the reactants in the reactor inlet is generally between 50° and 80° C. and the temperature of the products flowing out is generally between 130° and 200° C., preferably between 140° and 180° C.

The continuous adiabatic polynitration by the process of the present invention can be achieved with all aromatic compounds. Preferred aromatic compounds include: toluene, benzene, chlorobenzene and xylene.

The mixture of products dissolved in the sulfuric acid is not completely removed by the recirculation of the sulfuric acid after recovery. Dissolved organic products are therefore returned to the reactor together with the recirculated sulfuric acid. This recirculation of the product does not interfere with the conduct of the reaction in accordance with the present invention.

The heat of reaction of the first nitration together with the intimate first mixing and repeated redispersion are used to lower the water-binding constituents in the nitronium ion solution to be used in the second nitration. In a preferred embodiment of the present invention, the sulfuric acid content of the mixed acid can be decreased by from 1 to 10 wt. % as compared with an isothermal process. Further, in the adiabatic procedure, the heat of reaction can be used entirely for the separation of the product water from the mixed acid. This makes polynitration by this method particularly favorable with respect to energy efficiency.

The present invention is explained in more detail below by means of Examples and the drawings.

Figure 2:
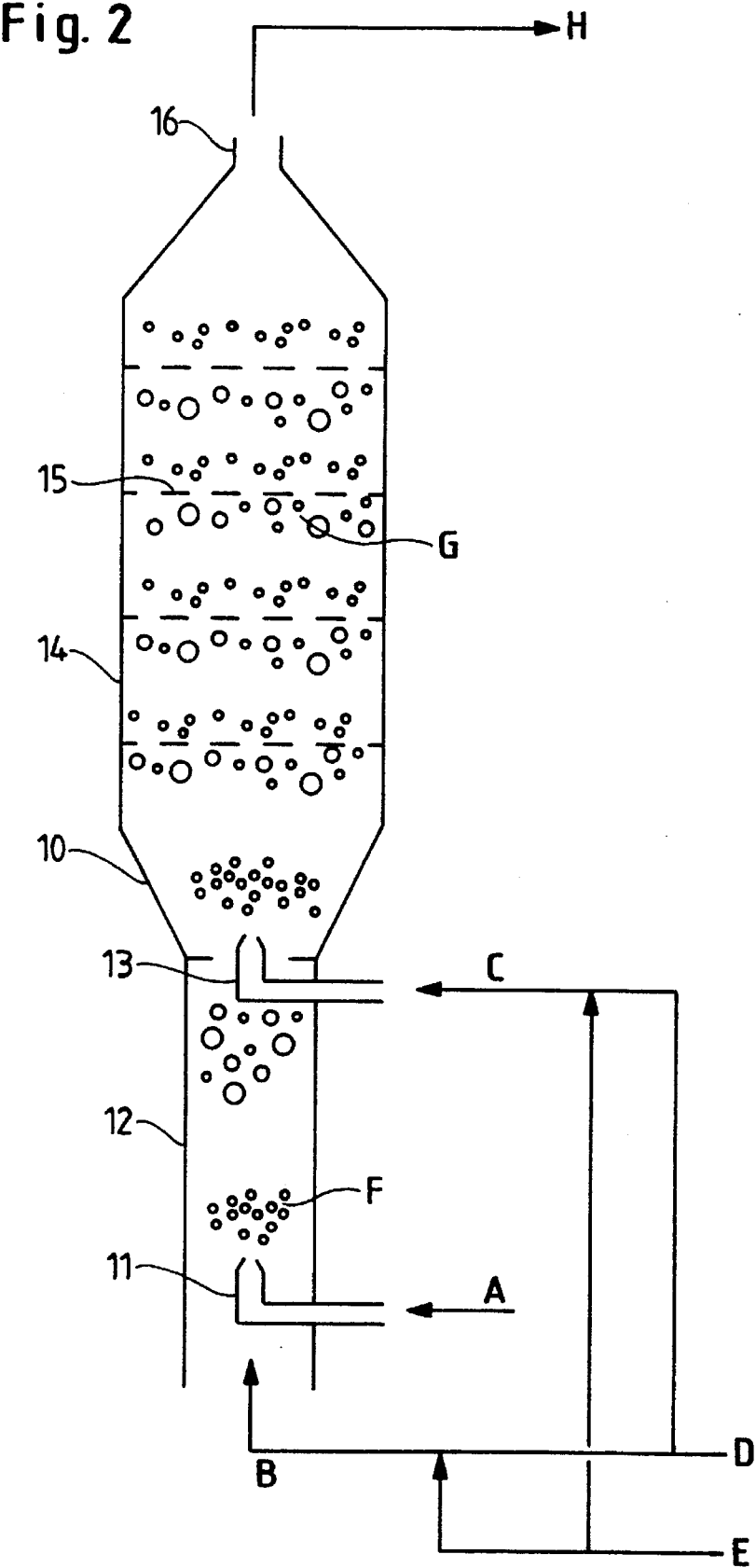
FIG. 2 is a diagram of a multistage tubular reactor system which is useful for carrying out the process of the present invention.

FIG. 1 is a diagram of a process for the adiabatic dinitration in a two-stage nozzle tubular reactor system useful for carrying out the process of the present invention. FIG. 2 is a diagram of a process for the adiabatic dinitration in a multistage tubular reactor system useful for carrying out the process of the present invention.

In the system shown in FIG. 1, liquid stream A made up of an aromatic compound is forced by means of a pump 1 through heat exchanger 2 into the two-stage nozzle tubular reactor system 3. The educt A is brought to the desired temperature in the heat exchanger 2. Liquid stream B which is a nitronium ion solution is forced by means of pump 4 through heat exchanger 5 into two-stage nozzle tubular reactor system 3. The two-stage nozzle tubular reactor system 3 is made up of nozzle 6 which finely disperses the two immiscible streams in each other, hold-up tube 7, redispersing nozzle 8 and another hold-up tube 9. The product stream C which is composed of an aqueous phase and an organic phase passes out of the reactor system.

Nozzle 6 is a jet mixer which provides immediate intimate mixing of the two phases at the nozzle outlet, disperses the organic phase and emulsifies the organic phase in the aqueous phase through the high local energy input. At the same time, the exothermic reaction of the educts A and B which proceeds in hold-up tube 7, is initiated. The dinitration proceeds in several successive reaction steps, with nitronium ions being added successively to the aromatic ring. As the number of nitro groups on the aromatic ring increases, the aromatic ring is deactivated so that the nitration rate falls increasingly sharply. Due to a coalescence of the organic liquid droplets, the specific surface area of the emulsion decreases so that redispersion is necessary in order to maintain a high nitration rate. In redispersing nozzle 8 which follows hold-up tube 7, the organic liquid droplets are again dispersed to form a fine emulsion in the aqueous phase. The nitration reaction is continued in hold-up tube 9. Further redispersing and hold-up stages may optionally be arranged after nozzle 8 and hold-up tube 9 to ensure a complete conversion of the aromatic compound. The product mixture obtained is made up of aqueous residual nitronium ion solution and aromatic phase. This product mixture may be subsequently worked up in known manner. (See, for example, DE-A 4,238,390).

In the system shown in FIG. 2, the dinitration of an aromatic compound is carried out in nozzle tubular reactor 10 with multistage redispersion and initial intensive dispersion of the two immiscible liquid streams. The stream of aromatic compound A is passed via jet mixer 11 into the stream of nitronium ion solution B. The nitronium ion solutions B and C may be prepared by mixing aqueous nitric acid (stream D) together with an aqueous auxiliary solution (stream E). The aqueous nitric acid of stream D preferably has an $HNO_3$ content of between 50 and 100 wt. %. The aqueous auxiliary solution of stream E preferably includes water and $H_2SO_4$, but may also include or be made up of $H_3PO_4$, $CH_3COOH$, perchloric acid and trifluoromethanesulfonic acid. The liquid stream of aromatic compound A is dispersed in the nitronium ion solution of stream B in jet mixer 11 of nozzle tubular reactor 10 and a finely dispersed emulsion F is formed. The reaction between aromatic compound and nitronium ions starts spontaneously as soon as the two immiscible liquids in streams A and B come into contact. The fine emulsion F created by the input of kinetic energy provides, by means of its high phase interface, for a high nitration rate. This nitration rate declines as the droplets of organic liquid coalesce.

While the first nitro group is added to the aromatic compound very rapidly in the short hold-up tube in the lower stage 12 of the reactor, the subsequently added nitro groups require a longer residence time and more severe nitrating conditions for addition to the aromatic compound. In order to maintain a high conversion rate, the coalesced two-phase stream G must be repeatedly dispersed in the reaction chamber. The far more difficult dinitration and trinitration are favored by the exothermic nature of the nitration reactions during the adiabatic operation of the nozzle tubular reactor. To intensify the nitrating conditions, fresh nitronium ion solution C may optionally be distributed in reactor 10 by means of second jet mixer 13. This addition of more nitronium ion solution or of highly concentrated sulfuric acid in a manner similar to that by which stream C is introduced may optionally be repeated in the upper stage of the reactor. The composition of solution C will generally not be identical to that of solution B and will preferably have a higher concentration of $HNO_3$. In second stage 14 of the reactor the coalesced droplets G of the aromatic compound are repeatedly dispersed into finely-dispersed droplets F by means of redispersing units 15 (e.g., perforated plates). The dispersed product H is obtained via reactor outlet 16. The dispersed product which is made up of aqueous residual nitronium ion solution and aromatic phase is subsequently worked up in known manner. (See, e.g., DE-A 4,238,390.)

The processing and reaction conditions maintained in the reaction systems illustrated in FIG. 1 and FIG. 2 are further explained below by means of Examples. All percentages reported in these Examples are percentages by weight, unless otherwise indicated.

EXAMPLES

A three-stage nozzle tubular reactor substantially similar to that shown in FIG. 1 was used in the Examples which follow. In each of these Examples, the educt streams were made up of a pure aromatic compound and of a nitronium ion solution which was prepared by mixing aqueous nitric acid with aqueous sulfuric acid ("mixed acid"). The educt streams were added in the manner described with respect to the system illustrated in FIG. 1 and controlled by a thermostat. The nozzle tubular reactor was insulated in order to avoid a loss of temperature during adiabatic operation. The composition of the mixed acid was determined gravimetrically. After separation of the aqueous and organic phases, the organic phase was first washed with 10% aqueous soda solution and then twice with water. The organic phase recovered was analyzed by gas chromatography using a glass capillary column, with the amount of the components being determined in per cent surface area. Because of the adiabatic mode of operation, the reaction temperatures along the reactor system were determined entirely by the composition of the streams of substances, the degree of conversion and the temperature of the educts. In each case, a dispersing nozzle together with a tandem-arranged holdup tube is referred to as a reaction stage.

Example 1

A three-stage nozzle tubular reactor equipped with a first mixing nozzle having an internal diameter of 0.3 mm and two redispersing nozzles having internal diameters of 0.3 mm was used. A hold-up tube of 60 mm in length and having an internal diameter of 4 mm was installed behind each nozzle. The educt temperature in each case was 120° C. prior to mixing and the two streams were as follows: 112.4 ml/h (97.4 g/h=1.06 mol/h) of toluene and 2500 ml/h (4330 g/h=2.27 mol/h) of a nitrating acid having the composition 78.3:3.3:18.4 (wt. % of $H_2SO_4:HNO_3:H_2O$).

The distribution of products after the first, second and third reactor stages (in each case after passing through the nozzle and hold-up distance) were measured by gas chromatography. The results of this analysis are reported in Table 1. (MNT=mononitrotoluene, DNT=dinitrotoluene, TNT=trinitrotoluene, remainder: by-products).

TABLE 1

|  | First Stage | Second Stage | Third Stage |
| --- | --- | --- | --- |
| 2-MNT | 6.6% | 0.3% | — |
| 3-MNT | 0.9% | 0.1% | — |

TABLE 1-continued

|  | First Stage | Second Stage | Third Stage |
| --- | --- | --- | --- |
| 4-MNT | 4.7% | 0.5% | — |
| 2,6-DNT | 16.7% | 18.8% | 19.0% |
| 2,5-DNT | 0.9% | 1.1% | 1.1% |
| 2,4-DNT | 65.0% | 73.6% | 74.0% |
| 2,3-DNT | 1.9% | 2.2% | 2.3% |
| 3,4-DNT | 2.8% | 3.3% | 3.4% |
| 2,4,6-TNT | — | — | — |

Example 2

The reactor used was the same as that which was used in Example 1. The educt temperature was 70° C. in each case and the two streams of were as follows: 315.7 ml/h (273.7 g/h=2.97 mol/h) of toluene and 4000 ml/h (6924 g/h=6.37 mol/h) of a nitrating acid of the composition 76.9:5.8:17.3 (wt. % of $H_2SO_4:HNO_3:H_2O$).

The distribution of products after the first, second and third reactor stages (in each case after passing through the nozzle and hold-up distance) were measured by gas chromatography. The results of these measurements are reported in Table 2. (MNT=mononitrotoluene, DNT=dinitro-toluene, remainder: by-products)

TABLE 2

| Reactor stage | Total MNT | Total DNT |
| --- | --- | --- |
| 1 | 26.5% | 73.4% |
| 2 | 16.7% | 83.2% |
| 3 | 9.1% | 90.8% |

Example 3

The three-stage nozzle tubular reactor used in Example 1 was modified by substituting a first mixing nozzle having an internal diameter of 0.2 mm and a redispersing nozzle having an internal diameter of 0.2 mm for the first mixing nozzle in the Example 1 device. Behind the first nozzle, a hold-up tube of 605 mm in length was installed. Behind the second nozzle, a hold-up tube of 605 mm in length was installed. Each of these hold-up tubes had an internal diameter of 2 mm. Behind these hold-up tubes was installed another hold-up tube of 2300 mm in length having an internal diameter of 1.76 mm. The educt temperature was 120° C. in each case and the streams were as follows: 301.8 ml/h (261.6 g/h=2.84 mol/h) of toluene and 5500 ml/h (9423.7 g/h=5.38 mol/h) of nitrating acid having the composition 77.0:3.6:19.4 (wt. % of $H_2SO_4:HNO_3:H_2O$).

The distribution of products after the third reactor stage was measured by gas chromatography. The results of this measurement are reported in Table 3. (MNT=mononitrotoluene, DNT=dinitrotoluene, remainder: by-products)

TABLE 3

| Reactor stage | Total MNT | Total DNT |
| --- | --- | --- |
| 3 | 13.2% | 86.5% |

Example 4

The three-stage nozzle tubular reactor used in Example 1 was modified by substituting the first mixing nozzle with a nozzle having an internal diameter of 0.2 mm, a tandem-arranged hold-up tube of 550 mm in length having an internal diameter of 2 mm and two redispersing nozzles having an internal diameter of 0.3 mm each of which was equipped with a tandem-arranged hold-up tube 220 mm in length having an internal diameter of 2 mm. The educt temperature was 120° C. in each case and the streams were as follows: 121.3 ml/h (104.88 g/h=1.14 mol/h) of toluene and 2500 ml/h (4283.5 g/h=2.45 mol/h) of a nitrating acid having the composition 77.0:3.6:19.4 (wt. % of $H_2SO_4$:$HNO_3$:$H_2O$).

The distribution of products after the first, second and third reactor stages (in each case after passing through the nozzle and hold-up distance) were measured by gas chromatography. These measurements are reported in Table 4. (MNT=mononitrotoluene, DNT=dinitro-toluene, remainder: by-products)

TABLE 4

| Reactor stage | Total MNT | Total DNT |
| --- | --- | --- |
| 1 | 29.9% | 69.9% |
| 2 | 8.6% | 91.3% |
| 3 | 4.7% | 95.2% |

Example 5

The reactor used in Example 4 was also used in this Example. The educt temperature was 120° C. in each case and the streams were as follows: 167.8 g/h (=1.82 mol/h) of toluene and 6853.6 g/h (=3.92 mol/h) of a nitrating acid having the composition 77.0:3.6:19.4 (wt. % of $H_2SO_4$:$HNO_3$:$H_2O$).

The distribution of products after the first, second and third reactor stages (in each case after passing through the nozzle and hold-up distance were measured by gas chromatography. The results of these measurements are reported in Table 5. (MNT=mononitrotoluene, DNT=dinitro-toluene, remainder: by-products)

TABLE 5

| Reactor stage | Total MNT | Total DNT |
| --- | --- | --- |
| 1 | 28.1% | 71.6% |
| 2 | 9.0% | 90.8% |
| 3 | 5.1% | 94.8% |

Example 6

The same reactor used in Example 4 was used in this Example. The educt temperature was 120° C. in each case and the streams were as follows: 230.7 g/h (=2.51 mol/h) of toluene and 9423.7 g/h (=5.38 mol/h) of nitrating acid having the composition 77.0:3.6:19.4 (wt. % of $H_2SO_4$:$HNO_3$:$H_2O$).

The distribution of products after the first and second reactor stages (in each case after passing through the nozzle and hold-up distance) were measured by gas chromatography. The results of this analysis are reported in Table 6. (MNT=mononitrotoluene, DNT=dinitro-toluene, remainder: by-products)

TABLE 6

| Reactor stage | Total MNT | Total DNT |
| --- | --- | --- |
| 1 | 27.5% | 72.4% |
| 2 | 10.3% | 88.9% |

Example 7

The reactor used in Example 4 was modified to include two additional redispersing nozzles behind the mixing nozzle and the two existing redispersing nozzles. These additional redispersing nozzles had an internal diameter of 0.3 mm and were each connected to a hold-up tube of 550 mm in length with an internal diameter of 2 mm. The educt temperature was 140° C. in each case and the streams were as follows: 78.0 g/h (=1.0 mol/h) of benzene and 2500 g/h (=2.3 mol/h) of nitrating acid having the composition 78.6:5.8:15.6 (wt. % of $H_2SO_4$:$HNO_3$:$H_2O$).

The distribution of products after the sixth reactor stage was measured by gas chromatography. The results of this analysis are reported in TABLE 7. (MNB=mononitrobenzene, DNB=dinitrobenzene, remainder: by-products)

TABLE 7

| Reactor stage | Total MNT | Total DNT |
| --- | --- | --- |
| 6 | 1.3% | 98.7% |

Example 8

The reactor used in Example 7 was also used in this Example. The educt temperature was 135° C. in each case and the streams were as follows: 112.5 g/h (=1.0 mol/h) of chlorobenzene and 2500 g/h (=2.3 mol/h referred to $HNO_3$) of nitrating acid having the composition 81.5:5.8:12.7 (wt. % of $H_2SO_4$:$HNO_3$:$H_2O$).

The distribution of products after the sixth reactor stage was measured by gas chromatography. The results of this analysis are reported in Table 8. (MNCB=mononitrochlorobenzene, DNCB=dinitrochlorobenzene, remainder: by-products)

TABLE 8

| Reactor stage | Total MNT | Total DNT |
| --- | --- | --- |
| 6 | 78.2% | 21.6% |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A continuous process for the polynitration of an aromatic compound in liquid form comprising reacting the aromatic compound with a nitronium ion solution in a manner such that
   a) the polynitration is carried out in a single reaction apparatus under adiabatic conditions in an emulsion as the reaction medium,
   b) from about 1.3 to about 3.5 mol of $HNO_3$ per mol of aromatic compound is fed in the form of a nitronium ion solution to the reaction apparatus,
   c) the emulsion is maintained by repeated dispersion to reduce coalescence,
   d) the time in which the streams of aromatic compound and nitronium ion solution stream are first dispersed is less than one second, and
   e) at least 20% of the total amount of $HNO_3$ is present at the time the aromatic compound and nitronium ion solution are first dispersed.

2. The process of claim 1 in which the total amount of nitronium ion solution is present at the time that solution is first dispersed with the aromatic compound.

3. The process of claim 1 in which the nitronium ion solution is a mixed acid composed of sulfuric acid and nitric acid.

4. The process of claim 1 in which from 1.5 to 3.0 mol of $HNO_3$ per mol of aromatic compound is present in the nitronium ion solution.

5. The process of claim 1 in which from 1.7 to 2.5 mol of nitric acid per mol of aromatic compound is present in the nitronium ion solution.

6. The process of claim 1 in which the aromatic compound and nitronium ion solution are first dispersed in a jet mixer with an energy input of from 10 to 10,000 joules per liter to produce an emulsion.

7. The process of claim 1 in which the aromatic compound and nitronium ion solution are first dispersed in a jet mixer with an energy input of from 50 to 2,000 J/l to produce an emulsion.

8. The process of claim 1 in which the aromatic compound and nitronium ion solution are first dispersed in a jet mixer with an energy input of from 100 to 1,000 J/l to produce an emulsion.

9. The process of claim 1 in which the emulsion is repeatedly redispersed by means of at least one jet mixer, at least one static mixer or at least one dynamic mixer.

10. The process of claim 9 in which the redispersion is conducted with an energy input of from 1 to 1,000 joules per liter.

11. The process of claim 9 in which the redispersion is conducted with an energy input of from 10 to 200 J/l.

12. The process of claim 1 in which the nitronium ion solution is made up of (1) from about 80 to 100 wt. % of inorganic constituents which are composed of
   (i) from about 60 to about 95 wt. % of $H_2SO_4$,
   (ii) from about 1 to about 20 wt. % of $HNO_3$ and
   (iii) at least 3 wt. % of $H_2O$ and (2) up to 20 wt. % of organic constituents which are composed of
   (i) from about 70 to about 100 wt. % of polynitrated aromatics and
   (ii) from about 0 to about 30 wt % of by-products.

13. The process of claim 1 in which the aromatic compound and nitronium ion solution are mixed at a temperature between 80° and 150° C.

14. The process of claim 1 in which the aromatic compound and nitronium ion solution are mixed at a temperature between 100° and 130° C.

15. The process of claim 1 in which the reaction mixture leaves the reaction apparatus at a temperature of from 130° to 200° C.

16. The process of claim 1 in which the reaction mixture leaves the reaction apparatus at a temperature of from 140° to 180° C.

17. The process of claim 1 in which the aromatic compound and nitronium ion solution are mixed at a temperature between 50° and 80° C. and the reactants leave the reaction apparatus at a temperature of from 130° to 200° C.

18. The process of claim 1 in which the aromatic compound and nitronium ion solution are mixed at a temperature between 50° and 80° C. and the reactants leave the reaction apparatus at a temperature of from 140° to 180° C.

19. The process of claim 1 in which the aromatic compound is toluene, benzene, chlorobenzene or xylene.

* * * * *